United States Patent [19]
Naito et al.

[11] Patent Number: 5,972,244
[45] Date of Patent: Oct. 26, 1999

[54] TOLAN COMPOUND AND LIQUID CRYSTAL COMPOSITION CONTAINING THE SAME

[75] Inventors: Tomijiro Naito, Asaka; Kikuo Yamamoto, Habikino; Katsuji Niino, Kawanishi; Yumiko Sakamaki, Sayama, all of Japan

[73] Assignee: Citizen Watch Co., Ltd., Tokyo, Japan

[21] Appl. No.: 09/005,686

[22] Filed: Jan. 13, 1998

[30] Foreign Application Priority Data

| Jan. 14, 1997 | [JP] | Japan | ................................... | 9-004483 |
| Jan. 14, 1997 | [JP] | Japan | ................................... | 9-004484 |
| Jan. 14, 1997 | [JP] | Japan | ................................... | 9-004485 |

[51] Int. Cl.[6] .......................... C09K 19/20; C09K 19/30; C07C 69/76
[52] U.S. Cl. ............................... 252/299.67; 252/299.63; 560/62; 560/65
[58] Field of Search ..................... 252/299.61, 299.63, 252/299.64, 299.65, 299.66, 299.67; 560/62, 65

[56] References Cited

U.S. PATENT DOCUMENTS 5,656,198  8/1997  Naito et al. ........................ 252/299.01

FOREIGN PATENT DOCUMENTS

| 3-145450 | 6/1991 | Japan . |
| 08333305 | 12/1996 | Japan . |
| 09059219 | 3/1997 | Japan . |
| 09118651 | 5/1997 | Japan . |

*Primary Examiner*—Shean C. Wu
*Attorney, Agent, or Firm*—Oblon, Spivak, McClelland, Maier & Neustadt, P.C.

[57] ABSTRACT

A novel tolan compound of the formula (I):

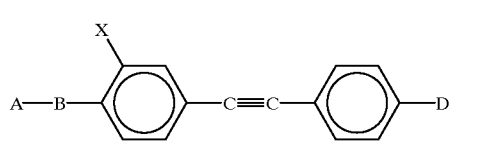

(I)

wherein A is $C_{1-10}$ alkyl, $C_{1-10}$ alkoxy, cyclohexyl substituted by $C_{1-10}$ alkyl at 4 position, cyclohexyl substituted by $C_{1-10}$ alkoxy group at 4 position or a group of the formula:

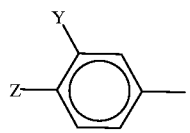

wherein Y is hydrogen or halogen and Z is $C_{1-10}$ alkyl or halogen; B is a single bond or —CO—O— or —O—CO—; D is hydrogen, $C_{1-10}$ alkyl, cyclohexyl substituted by $C_{1-10}$ alkyl at 4 position; and Z represents a hydrogen atom or a halogen atom. The tolan compound can increase the N-I point, decrease the viscosity, and increase the double refractive index of a liquid crystal composition without affecting the viscosity and threshold voltage Vth, and is mutually soluble with various other liquid crystal compounds, so that the compound can be used as a constituent of a liquid crystal composition in combination with these other liquid crystal materials to improve the properties of the composition.

9 Claims, 1 Drawing Sheet

FIG. 1

TOLAN COMPOUND AND LIQUID CRYSTAL COMPOSITION CONTAINING THE SAME

BACKGROUND OF THE INVENTION

1. Field of the Invention:

The present invention relates to a tolan compound which is useful as a liquid crystal material and to a liquid crystal composition containing this tolan compound. The present invention also relates to a liquid crystal display device using the liquid crystal composition containing this tolan compound.

2. Background Art:

A liquid crystal display device has been widely utilized for a watch, an electronic calculator, a word processor, a television set, and the like. Of these liquid crystal display devices, particularly frequently used is a liquid crystal display device which utilizes optical anisotropy and dielectric anisotropy of a liquid crystal material.

A wide liquid crystal temperature range, a low viscosity to ensure a rapid electro-optical response rate, a wide visual range, a suitable double refractive index (Δn) to provide a wide visual scope and a high contrast, a large dielectric anisotropy (Δε) to ensure a low driving voltage, and the characteristics to be chemically and optically stable are given as the characteristics required for a liquid crystal material to be used for liquid crystal display devices.

Liquid crystal compositions presently used are usually prepared by mixing a compound having a liquid crystal phase near room temperatures and a compound having a liquid crystal phase at temperatures higher than room temperatures. In order for a liquid crystal display device to be used outdoor the liquid crystal must be stable in the temperature range of −40° C. to 90° C. In addition, because of the temperature dependency of dielectric anisotropy and refractive index anisotropy, that is, because of occurrence of sudden change near the N-I point (nematic anisotropy phase transition temperature), it is necessary to use a liquid crystal material with a high N-I point.

Furthermore, to ensure a wide visual angle and a high contrast, the retardation of liquid crystal phase, Δn·d, wherein Δn is the double refractive index of the liquid crystal material and d is the thickness of liquid crystal layer, must be optimized. However, because the thickness of liquid crystal layer (d) is limited to a certain range and a high response rate is required for liquid crystal display devices actually used, the thickness of liquid crystal layer (d) tends to be thin. Because of this reason, a liquid crystal material with a large double refractive index (Δn) is required.

A liquid crystal material is also desired to have a low viscosity to achieve high speed operation. A rise time, indicated by $\tau_{on}$, when voltage is applied, and a fall time, indicated by $\tau_{off}$, when voltage is cut off, are given by the following equations:

$$\tau_{on} = \eta_{ii} d^2 (\epsilon_0 \Delta \epsilon V^2 - K\pi^2)^{-1}$$

$$\tau_{off} = \eta_{ii} d^2 / \pi^2 K$$

wherein $\eta_{ii}$ is a viscosity parameter, d is a thickness of a liquid crystal layer, $\epsilon_0$ is a dielectric constant in vacuum, Δε is an anisotropy of dielectric constant, V is an applied voltage, and K is a parameter in relation to a modulus of elasticity, which is represented by the equation:

$$K = k_{11} + (k_{33} - 2k_{22})/4$$

in which $k_{11}$, $k_{22}$, and $k_{33}$ are spray, twist, and bend modulus of elasticity respectively. Accordingly, in order to obtain a high response rate, the liquid crystal material must have a low viscosity. Use of a liquid crystal compound having a low viscosity is therefore indispensable.

A driving voltage is dependent on a threshold voltage Vth, whereas the threshold voltage Vth is inversely proportional to the square root of dielectric anisotropy (Δε). Accordingly, the threshold voltage Vth can be controlled low when a liquid crystal material with a positive value of dielectric anisotropy (Δε) is used.

Although various liquid crystal compounds have been developed and put on use up to the present time, there is no single liquid crystal compound satisfying all the characteristics mentioned above. Therefore, in practice, several kinds of liquid crystal compounds having different characteristics or non-liquid crystal compounds are mixed and used. Such mixtures, however, are not necessarily satisfactory.

4-Alkyl-4'-alkoxytolan (German Patent No. 2226376) and 4-alkyl-4'-fuluorotolan (Japanese Patent Application Laid-Open No. 260031/1986) are examples of known tolan compounds which are used mixed for the above-mentioned purpose. The mixtures of these tolan compounds, however, are not necessarily satisfactory.

As described above, in spite of various studies in the past on liquid crystal compositions, no material which sufficiently satisfies all above characteristics has been found. Each compound used for liquid crystal materials has merits and demerits in its characteristics. In addition, the degree of the above required characteristics is different according to the type of liquid crystal display devices. The development of a novel liquid crystal compound and a liquid crystal additive which can provide characteristics according to the intended object of a liquid crystal display device has been desired.

Accordingly, an object of the present invention is to provide a novel tolan compound which, if added to a liquid crystal composition, can raise the N-I point, reduce the viscosity, and increase the double refractive index (Δn) of the liquid crystal composition. Another object of the present invention is to provide such a liquid crystal composition comprising this novel tolan compound. Still another object of the present invention is to provide a liquid crystal display device using the liquid crystal composition.

SUMMARY OF THE INVENTION

Accordingly, a specific object of the present invention is to provide a tolan compound represented by the following formula (I):

wherein A represents an alkyl group having 1–10 carbon atoms, an alkoxy group having 1–10 carbon atoms, a cyclohexyl group which is substituted by an alkyl group having 1–10 carbon atoms at the 4 position thereof, a cyclohexyl group which is substituted by an alkoxy group having 1–10 carbon atoms at the 4 position thereof, or a group represented by the following formula, wherein Y represents a hydrogen atom or a halogen atom and Z represents an alkyl group having 1–10 carbon atoms or a halogen atom;

B represents a single bond or a group —CO—O— or —O—CO—;

D represents a hydrogen atom, an alkyl group having 1–10 carbon atoms, or a cyclohexyl group which is substituted by an alkyl group having 1–10 carbon atoms at the 4 position thereof; and X represents a hydrogen atom or a halogen atom.

Another object of the present invention is to provide a liquid crystal composition comprising at least one of the tolan compounds represented by the above formula (I).

Still another object of the present invention is to provide a liquid crystal display device using the liquid crystal composition.

Other objects, features and advantages of the invention will hereinafter become more readily apparent from the following description.

DETAILED DESCRIPTION OF THE INVENTION AND PREFERRED EMBODIMENTS

The tolan compounds (I) of the present invention include the compounds represented by the following formulae (Ia) to (Ic):

(Ia)

wherein $A_1$ represents a phenyl group which is substituted by an alkyl group having 1–10 carbon atoms at the 4 position thereof or a cyclohexyl group which is substituted by an alkyl group having 1–10 carbon atoms at the 4 position thereof and R represents an alkyl group having 1–10 carbon atoms;

(Ib)

wherein $B_1$ represents a single bond or a group —CO—O— and $A_2$ represents an alkyl group having 1–10 carbon atoms or an alkoxy group having 1–10 carbon atoms when $B_1$ is a single bond or represents a cyclohexyl group which is substituted by an alkyl group having 1–10 carbon atoms at the 4 position thereof or a cyclohexyl group which is substituted by an alkoxy group having 1–10 carbon atoms at the 4 position thereof when $B_1$ is a group —CO—O—; and (Ic)

wherein $B_2$ represents a group —CO—O— or —O—CO—, $A_3$ represents a cyclohexyl group which is substituted by an alkyl group having 1–10 carbon atoms at the 4 position thereof when $B_2$ is a group —CO—O— or represents a group represented by the following formula when $B_2$ is a group —O—CO—:

wherein Y and Z have the meanings defined above, and R has the meaning defined above.

The halogen atom which is present in the tolan compound (Ic) of the present invention as a substituent is preferably fluorine atom in view of the viscosity and specific resistance of the tolan compound, although chlorine atom and bromine atom are acceptable.

The processes for preparing the tolan compounds of the present invention will now be illustrated.

Process 1

The compounds represented by the general formula (Ia) is prepared according to the reaction scheme described below. First, an acid chloride (a) is reacted with a substituted phenol (b) in an inert organic solvent such as pyridine or the like. The reaction mixture is then recrystallized, washed with water, and dried to prepare an ester compound (c). Next, this ester compound (c) is reacted with an acetylene compound (d) in the presence of triethylamine or the like, followed by washing with water, drying, and recrystallizing to obtain a tolan compound (Ia).

wherein $A_1$ and R have the meanings defined above.

Process 2

Among the compounds represented by the general formula (Ib), those represented by the general formula (Ib'), which has a group —CO—O— for $B_1$ in the formula (Ib), can be prepared according to the reaction scheme described below. First, an acid chloride (a') is reacted with a substituted phenol (b') in an inert organic solvent such as pyridine or the like. The reaction mixture is then recrystallized, washed with water, and dried to prepare an ester compound (c'). Next, this ester compound (c') is reacted with phenyl acetylene (d') in the presence of triethylamine or the like, followed by washing with water, drying, and recrystallizing to obtain a tolan compound (Ib').

wherein $A_2$ has the meaning defined above.

Process 3

Among the compounds represented by the general formula (Ib), those represented by the general formula (Ib"), which has a single bond for $B_1$ in the formula (Ib), can be prepared according to the following reaction scheme by reacting a substituted bromobenzene (e) and a phenylacetylene (d') in the presence of triethylamine or the like, and washing with water, drying, and recrystallizing the resulting reaction product.

wherein $A_2$ has the meaning defined above.

Process 4

Among the compounds represented by the general formula (Ic), those represented by the general formula (Ic'), which has a group —CO—O— for $B_2$ in the formula (Ic), can be prepared according to the reaction scheme described below. First, an acid chloride (a") is reacted with a substituted phenol (b') in an inert organic solvent such as pyridine or the like. The reaction mixture is then recrystallized, washed with water, and dried to prepare an ester compound (c"). Next, this ester compound (c") is reacted with an acetylene compound (d") in the presence of triethylamine or the like, followed by washing with water, drying, and recrystallizing to obtain a tolan compound (Ic').

wherein $A_3$ and R have the meanings defined above.

Process 5

Among the compounds represented by the general formula (Ic), those represented by the general formula (Ic"), which has a group —O—CO— for $B_2$ in the formula (Ic), can be prepared according to the reaction scheme described below. First, bromobenzoic acid (e') is reacted with a halogenating agent such as thionyl chloride or the like to form an acid chloride (f). The acid chloride (f) is reacted with a substituted phenol (g) in an inert organic solvent such as pyridine or the like. The reaction mixture is then recrystallized, washed with water, and dried to prepare a phenyl ester substituted by bromobenzoic acid (h). Next, this compound (h) is reacted with alkylcyclohexylphenylacetylene (i) in the presence of triethylamine or the like, followed by washing with water, drying, and recrystallizing to obtain a tolan compound represented by the general formula (Ic"). A tolan compound (Ic") can be obtained in the same manner, even if the substituted phenol (g) is replaced by a substituted cyclohexanol.

wherein $A_3$ and R have the meanings defined above.

Among the tolan compounds of the present invention, the tolan compounds (Ia) and (Ic) are excellent compounds which, when added to a liquid crystal composition, can increase the N-I point and double refractive index ($\Delta n$) of the liquid crystal composition.

Also, among the tolan compounds of the present invention, the tolan compound (Ib) is an excellent compound which, when added to a liquid crystal composition, can increase double refractive index ($\Delta n$) without significantly changing the threshold voltage Vth of the liquid crystal composition. In addition, among the tolan compounds (Ib), tricyclic compounds can increase the N-I point and dicyclic compounds can decrease viscosity, demonstrating that the both are excellent compounds.

Therefore, the tolan compound of the present invention can be mixed with various liquid crystal compounds to produce a liquid crystal composition. Examples of the liquid crystal compounds which can be mixed with the tolan compound of the present invention include esters, cyclohexylphenyl compounds, biphenyl compounds, pyrimidine compounds, dioxane compounds, tolan compounds, and the like. Either one of these liquid crystal compounds or a mixture of two or more of these compounds may be used and blended with the tolan compound of the present invention.

The proportion of the tolan compound used in the liquid crystal composition of the present invention cannot be generically decided and differs according to the types and proportions of other liquid crystal compounds which are used together. Generally, a proportion in the range of 1 to 50% by weight, and more preferably 3 to 20% by weight is applicable.

As mentioned above, the liquid crystal composition containing the tolan compound of the present invention has excellent properties as a liquid crystal material. The liquid crystal display device using this liquid crystal composition has a wide temperature range and a wide visible angle.

Other features of the invention will become apparent in the course of the following description of the exemplary embodiments which are given for illustration of the invention and are not intended to be limiting thereof. The threshold voltage in test examples hereinafter was measured for the liquid crystal composition installed in a TN-Type liquid crystal display with a cell thickness of 9 µm.

EXAMPLES

Example 1

Figure 1:
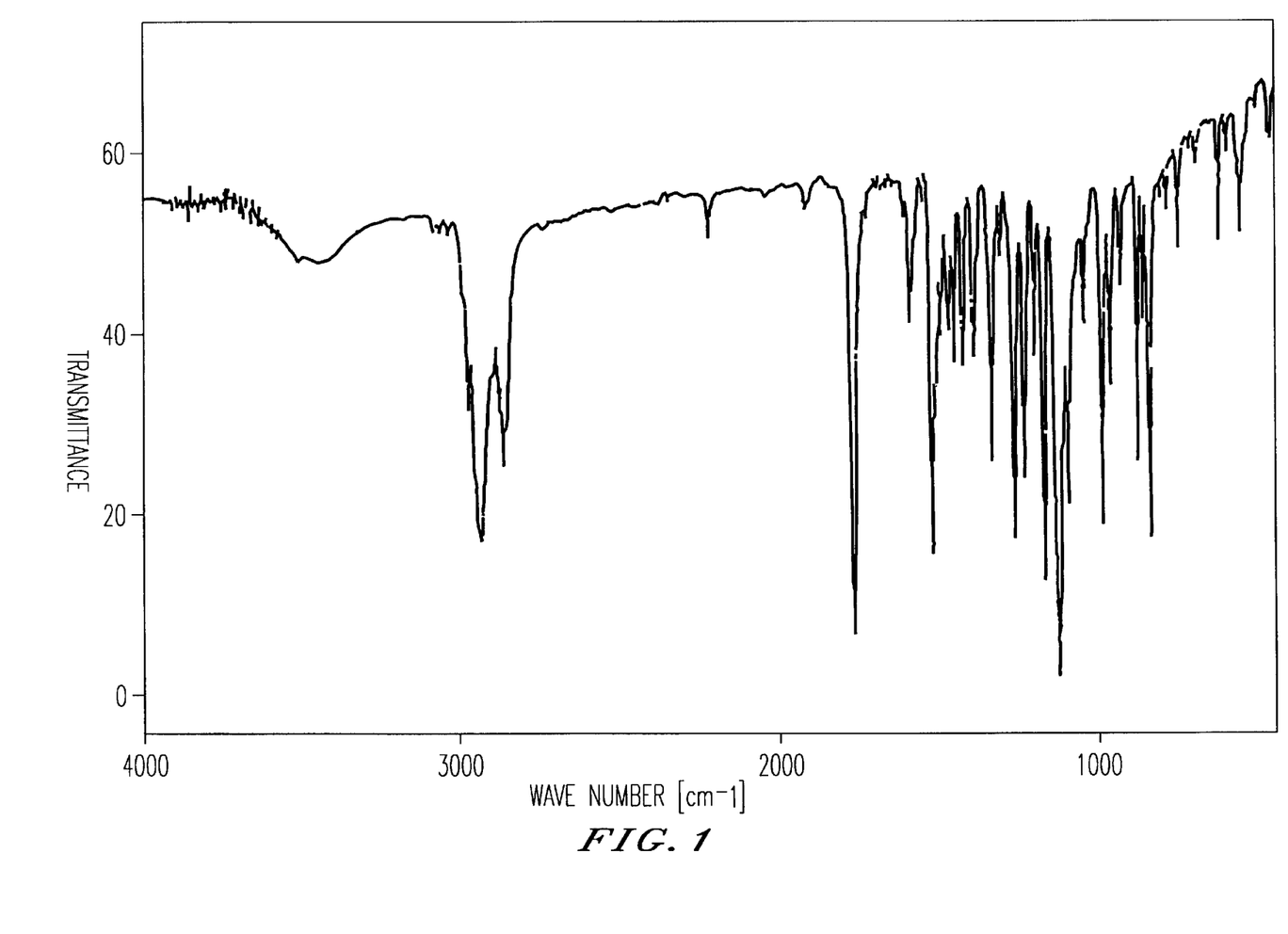
FIG. 1 is a diagram showing an infrared absorption spectrum of the tolan compound prepared in Example 1.

29 g of 2-fluoro-4-bromophenol, 100 ml of dimethylformamide, and 13 g of pyridine were dissolved. 29 g of commercially available trans-4-n-propylcyclohexanecarboxylic acid chloride was added dropwise to the mixture, which was then stirred with heating. The reaction mixture was charged into water to produce crystals. The crystals were then collected by filtration, washed with dilute hydrochloric acid and water, and dried in vacuum. The dry product was recrystallized from a mixed solvent of ethyl acetate and methanol to prepare 45 g of 2-fluoro-4-bromophenyl trans-4-n-propylcyclohexane carboxylate. To this product were added 23 g of 4-ethylphenylacetylene, 0.09 g of bis(triphenylphosphine)palladium (II) chloride, 0.1 g of copper iodide, 0.79 g of triphenylphosphine, and 250 ml of triethylamine. This mixture was stirred with heating. The reaction mixture was charged into water and neutralized with hydrochloric acid to produce crystals. The crystals were collected by filtration, washed with water, and dried in vacuum. The dry product was recrystallized from a mixed solvent of ethyl acetate and methanol to prepare 33 g of a compound shown by the following structural formula. This compound had a nematic liquid crystal phase, a C-N point (crystal-nematic phase transition temperature) of 100° C., and an N-I point of 202° C. The IR spectrum of this compound is shown in FIG. 1.

Example 2

34 g of a compound with the structural formula described below was prepared in the same manner as in Example 1, except for using 28 g of 4-butylphenylacetylene instead of 23 g of 4-ethylphenylacetylene. This compound had a nematic liquid crystal phase, a C-N point (crystal-nematic phase transition temperature) of 64° C., and an N-I point of 194° C. The IR spectrum of this compound had peaks (cm$^{-1}$) at 3024, 2927, 2215, 1751, 1515, 1266, 1233, 1194, 1160, and 1127.

Example 3

37 g of a compound with the structural formula described below was prepared in the same manner as in Example 1, except for using 30 g of 4-pentylphenylacetylene instead of 23 g of 4-ethylphenylacetylene. This compound had a nematic liquid crystal phase, a C-N point (crystal-nematic phase transition temperature) of 70° C., and an N-I point of 193° C. The IR spectrum of this compound had peaks (cm$^{-1}$) at 3020, 2930, 2215, 1759, 1514, 1260, 1229, 1192, 1156, and 1116.

Example 4

35 g of a compound with the structural formula described below was prepared in the same manner as in Example 1, except for using 26 g of 4-propylphenylacetylene instead of 23 g of 4-ethylphenylacetylene and 31 g of trans-4-n-butylcyclohexanecarboxylic acid chloride instead of 29 g of trans-4-n-propylcyclohexanecarboxylic acid chloride. This compound had a nematic liquid crystal phase, a C-N point (crystal-nematic phase transition temperature) of 68° C., and an N-I point of 198° C. The IR spectrum of this compound had peaks (cm$^{-1}$) at 3020, 2931, 2225, 1759, 1514, 1264, 1230, 1193, 1158, and 1120.

Example 5

33 g of a compound with the structural formula described below was prepared in the same manner as in Example 1, except for using 26 g of 4-ethylbenzoic acid chloride instead of 29 g of trans-4-n-propylcyclohexanecarboxylic acid chloride. This compound had a nematic liquid crystal phase, a C-S point (crystal-smectic phase transition temperature) of 86° C., a S-N point (smectic-nematic phase transition temperature) of 133° C., and an N-I point of 180° C. The IR spectrum of this compound had peaks (cm$^{-1}$) at 3031, 2968, 2209, 1735, 1515, 1260, 1230, 1193, 1176, and 1122.

Test Example 1

A liquid crystal composition was prepared by blending 90 parts by weight of a commercially available nematic liquid crystal composition, ZLI-1132 (a product of Merck), and 10 parts by weight of the tolan compound of the present invention prepared in Example 1. The properties of the liquid crystal composition are shown in the following Table 1.

The properties of the liquid crystal composition composed only of ZLI-1132 are as follows:

N-I point: 72.0° C.

$\Delta n$: 0.138

Viscosity: 27.9 cP

Vth: 1.83 V

Liquid crystal compositions were prepared in the same manner as in the Test Example 1 from 90 parts by weight of the liquid crystal composition ZLI-1132 (a product of Merck) and 10 parts by weight of the tolan compounds of the present invention prepared in Examples 2–5. The properties of the liquid crystal compositions are shown in Table 1.

In addition to the number of the examples, the chemical formulae of the tolan compounds of the present invention for preparing the compositions are shown in Table 1. The properties of the liquid crystal composition composed only of ZLI-1132 are also described.

TABLE 1

| Example No. | Compounds | N-I (° C.) | $\Delta n$ at 25° C. | Viscosity (cP) at 20° C. | Vth(V) at 25° C. |
|---|---|---|---|---|---|
| Example 1 | ![structure] | 82.7 | 0.142 | 27.9 | 1.89 |

TABLE 1-continued

| Example No. | Compounds | N-I (° C.) | Δn at 25° C. | Viscosity (cP) at 20° C. | Vth(V) at 25° C. |
|---|---|---|---|---|---|
| Example 2 | C₃H₇—⟨H⟩—COO—⟨F⟩—C≡C—⟨⟩—C₄H₉ | 82.3 | 0.144 | 27.8 | 1.88 |
| Example 3 | C₃H₇—⟨H⟩—COO—⟨F⟩—C≡C—⟨⟩—C₅H₁₁ | 83.2 | 0.144 | 27.7 | 1.85 |
| Example 4 | C₄H₉—⟨H⟩—COO—⟨F⟩—C≡C—⟨⟩—C₃H₇ | 82.2 | 0.145 | 27.9 | 1.82 |
| Example 5 | C₂H₅—⟨⟩—COO—⟨F⟩—C≡C—⟨⟩—C₂H₅ | 80.2 | 0.152 | 29.9 | 1.92 |
| Base Liquid Crystal | ZLI-1132 only | 72.0 | 0.138 | 27.9 | 1.83 |

As can be seen from Table 1, the tolan compounds of the present invention increase the N-I point and double refractive index (Δn) of the liquid crystal compositions which contain these compounds without giving no adverse effects on the viscosity and threshold voltage Vth of such compositions.

Example 6

26 g of 4-bromophenol, 100 ml of dimethylformamide, and 13 g of pyridine were dissolved. 29 g of commercially available trans-4-n-propylcyclohexanecarboxylic acid chloride was added dropwise to the mixture, which was then stirred with heating. The reaction mixture was charged into water to produce crystals. The crystals were collected by filtration, washed with dilute hydrochloric acid, and water and dried in vacuum. The dry product was recrystallized from a mixed solvent of ethyl acetate and methanol to prepare 44 g of 4-bromophenyl trans-4-n-propylcyclohexane carboxylate. To this product were added 18 g of phenylacetylene, 0.09 g of bis(triphenylphosphine) palladium (II) chloride, 0.1 g of copper iodide, 0.79 g of triphenylphosphine, and 200 ml of triethylamine. This mixture was stirred with heating. The reaction mixture was charged into water and neutralized with hydrochloric acid to produce crystals. The crystals were collected by filtration, washed with water, and dried in vacuum. The dry product was recrystallized from a mixed solvent of ethyl acetate and methanol to prepare 32 g of a compound shown by the following structural formula. This compound had a nematic liquid crystal phase, a C-N point (crystal-nematic phase transition temperature) of 10° C., and an N-I point of 148° C. The IR spectrum of this compound had peaks (cm⁻¹) at 3056, 2928, 2218, 1742, 1507, 1252, 1220, 1167, and 1130.

Example 7

To 26 g of 4-ethylbromobenzene were added 18 g of phenylacetylene, 0.09 g of bis (triphenylphosphine) palladium (II) chloride, 0.1 g of copper iodide, 0.79 g of triphenylphosphine, and 200 ml of triethylamine. This mixture was stirred with heating. The reaction mixture was charged into water and neutralized with hydrochloric acid to produce crystals. The crystals were collected by filtration, washed with water, and dried in vacuum. The dry product was recrystallized from a mixed solvent of ethyl acetate and methanol to prepare 20 g of a compound shown by the following structural formula. This compound had a melting point of 11° C. The IR spectrum of this compound had peaks (cm⁻¹) at 3079, 3056, 3030, 2966, 2931, 2872, 2217, and 1512.

Example 8

23 g of a compound with the structural formula described below was prepared in the same manner as in Example 7, except for using 32 g of 4-pentylbromobenzene instead of 26 g of 4-ethylbromobenzene. This compound had amelting point of 16° C. The IR spectrum of this compound had peaks (cm⁻¹) at 3079, 3056, 3030, 2956, 2929, 2857, 2218, and 1510.

Test Example 2

A liquid crystal composition was prepared by blending 90 parts by weight of a commercially available nematic liquid crystal composition, ZLI-1132 (a product of Merck), and 10 parts by weight of the tolan compound of the present invention prepared in Example 6. The properties of the liquid crystal composition are shown in the following Table 2.

The properties of the liquid crystal composition composed only of ZLI-1132 are as follows:

N-I point: 72.0° C.

Δn: 0.138

Viscosity: 27.9 cP

Vth: 1.83 V

Liquid crystal compositions were prepared in the same manner as in the Test Example 2 from 90 parts by weight of the liquid crystal composition ZLI-1132 (a product of Merck) and 10 parts by weight of the tolan compounds of the present invention prepared in Examples 7 and 8.

Table 2 also shows the number of the examples and the chemical formulae of the tolan compounds of the present invention used for the compositions. The properties of the liquid crystal composition composed only of ZLI-1132 are also described.

of the liquid crystal compositions which contain these compounds without affecting the threshold voltage Vth of such compositions. In addition, the tricyclic compounds can increase the N-I point and the dicyclic compounds can decrease the viscosity.

Example 9

26 g of 4-bromophenol, 100 ml of dimethylformamide, and 13 g of pyridine were dissolved. 29 g of commercially available trans-4-n-propylcyclohexanecarboxylic acid chloride was added dropwise to the mixture, which was then stirred with heating. The reaction mixture was charged into water to produce crystals. The crystals were collected by filtration, washed with dilute hydrochloric acid and then water and dried in vacuum. The dry product was recrystallized from a mixed solvent of ethyl acetate and methanol to prepare 44 g of 4-bromophenyl trans-4-n-propylcyclohexane carboxylate. To this product were added 40 g of 4-propylcyclohexylphenylacetylene, 0.09 g of bis(triphenylphosphine)palladium (II) chloride, 0.1 g of copper iodide, 0.79 g of triphenylphosphine, and 400 ml of triethylamine. This mixture was stirred with heating. The reaction mixture was charged into water and neutralized with hydrochloric acid to produce crystals. The crystals were collected by filtration, washed with water, and dried in vacuum. The dry product was recrystallized from a mixed solvent of ethyl acetate and methanol to prepare 45 g of a compound shown by the following structural formula. This compound had a liquid crystal phase, a C-S point (crystal-smectic phase transition temperature) of 67° C., a S-N point (smectic-nematic phase transition temperature) of 161° C., and an N-I point of 235° C. The IR spectrum of this compound had

TABLE 2

| Example No. | Compounds | N-I (° C.) | Δn at 25° C. | Viscosity (cP) at 20° C. | Vth(V) at 25° C. |
|---|---|---|---|---|---|
| Example 6 | C₃H₇—⟨H⟩—COO—⟨⟩—C≡C—⟨⟩ | 80.9 | 0.145 | 28.7 | 1.97 |
| Example 7 | C₂H₅—⟨⟩—C≡C—⟨⟩ | 60.3 | 0.141 | 22.7 | 1.73 |
| Example 8 | C₅H₁₁—⟨⟩—C≡C—⟨⟩ | 61.7 | 0.141 | 23.9 | 1.81 |
| Base Liquid Crystal | ZLI-1132 only | 72.0 | 0.138 | 27.9 | 1.83 |

As can be seen from Table 2, the tolan compounds of the present invention increase the double refractive index (Δn) peaks (cm⁻¹) at 3031, 2923, 2216, 1754, 1515, 1252, 1211, 1164, and 1125.

Example 10

47 g of a compound with the structural formula described below was prepared in the same manner as in Example 9, except for using 33 g of trans-4-n-pentylcyclohexanecarboxylic acid chloride instead of 29 g of trans-4-n-propylcyclohexanecarboxylic acid chloride. This compound had a liquid crystal phase, a C-S point (crystal-smectic phase transition temperature) of 86° C., a S-N point (smectic-nematic phase transition temperature) of 139° C., and an N-I point of 226° C. The IR spectrum of this compound had peaks (cm$^{-1}$) at 3031, 2922, 2146, 1745, 1515, 1244, 1204, 1160, and 1124.

Example 11

48 g of a compound with the structural formula described below was prepared in the same manner as in Example 9, except for using 35 g of trans-4-n-hexylcyclohexanecarboxylic acid chloride instead of 29 g of trans-4-n-propylcyclohexanecarboxylic acid chloride. This compound had a liquid crystal phase, a C-S point (crystal-smectic phase transition temperature) of 93° C., a S-N point (smectic-nematic phase transition temperature) of 133° C., and an N-I point of 235° C. The IR spectrum of this compound had peaks (cm$^{-1}$) at 3031, 2923, 2146, 1751, 1515, 1203, 1163, and 1122.

Example 12

120 g of thionyl chloride was added to 100 g of 4-bromobenzoic acid and the mixture was heated at 90° C. while stirring for 6 hours. After the reaction, an excess amount of thionyl chloride was removed by evaporation. 85 g of bromobenzoic acid chloride was obtained by vacuum distillation at about 20 mmHg in a distillation temperature range of 190–200° C. The bromobenzoic acid chloride was added dropwise to a solution prepared from 50 g of 3,4-difluorophenol, 150 ml of dimethylformamide, and 31 g of pyridine over about one hour while stirring at a temperature below 30° C. The mixture was then heated to 70° C. and stirred for 10 hours, and poured into a 10-fold amount of water to produce crystals. The crystals were collected by filtration, washed with dilute HCl and then water, dried in vacuum at 40° C., and recrystallized from ethyl acetate to obtain 50 g of 3,4-difluorophenyl 4-bromobenzoate. To this were added 40 g of 4-propylcyclohexylphenylacetylene, 0.11 g of bis(triphenylphosphine)palladium(II) chloride, 0.12 g of copper iodide, 0.96 g of triphenylphosphine, and 400 ml of triethylamine, followed by stirring for 10 hours while heating at 90° C. After the reaction, the reaction product was poured into a 10-fold amount of water to produce crystals. The crystals were collected by filtration, washed with water, dried in vacuum at 40° C., and recrystallized from a mixed solvent of ethyl acetate and methanol to obtain 43 g of a compound of the following formula. This compound had a nematic liquid crystal phase, a C-N point (crystal-nematic phase transition temperature) of 104° C., and an N-I point of 235° C. The IR spectrum of this compound had peaks (cm$^{-1}$) at 3030, 2921, 2217, 1735, 1518, 1246, 1178, 1145, and 1107.

Example 13

40 g of a compound with the structural formula described below was prepared in the same manner as in Example 12, except for using 41 g of 4-methylphenol instead of 50 g of 3,4-difluorophenol. This compound had a liquid crystal phase, a C-S point (crystal-smectic phase transition temperature) of 124° C., a S-N point (smectic-nematic phase transition temperature) of 132° C., and an N-I point of 235° C. The IR spectrum of this compound had peaks (cm$^{-1}$) at 3031, 2923, 2847, 2216, 1732, 1510, 1268, 1163, and 1137.

Test Example 3

A liquid crystal composition was prepared by blending 95 parts by weight of a commercially available nematic liquid crystal composition, ZLI-1132 (a product of Merck), and 5 parts by weight of the tolan compound of the present invention prepared in Example 9. The properties of the liquid crystal composition are shown in the following Table 3.

The properties of the liquid crystal composition composed only of ZLI-1132 are as follows:

N-I point: 72.0° C.
Δn: 0.138
Viscosity: 27.9 cP
Vth: 1.83 V

Liquid crystal compositions were prepared in the same manner as in the Test Example 3 from 95 parts by weight of the liquid crystal composition ZLI-1132 (a product of Merck) and 5 parts by weight of the tolan compounds of the present invention prepared in Examples 9–13. The properties of the liquid crystal compositions are shown in Table 3.

Table 3 also shows the number of the examples and the chemical formulae of the tolan compounds of the present invention used for the compositions. The properties of the liquid crystal composition composed only of ZLI-1132 are also described.

TABLE 3

| Example No. | Compounds | N-I (°C.) | Δn at 25° C. | Viscosity (cP) at 20° C. | Vth(V) at 25° C. |
|---|---|---|---|---|---|
| Example 9 | C3H7-[H]-COO-[B]-C≡C-[B]-[H]-C3H7 | 83.4 | 0.144 | 28.4 | 1.92 |
| Example 10 | C5H11-[H]-COO-[B]-C≡C-[B]-[H]-C3H7 | 83.1 | 0.145 | 28.1 | 1.87 |
| Example 11 | C6H13-[H]-COO-[B]-C≡C-[B]-[H]-C3H7 | 83.2 | 0.144 | 28.2 | 1.94 |
| Example 12 | C3H7-[H]-C≡C-[B]-COO-[B(F,F)] | 83.6 | 0.146 | 29.3 | 1.87 |
| Example 13 | C3H7-[H]-C≡C-[B]-COO-[B]-CH2 | 85.2 | 0.148 | 30.0 | 1.91 |
| Base Liquid Crystal | ZLI-1132 only | 72.0 | 0.138 | 27.9 | 1.83 |

As can be seen from Table 3, the tolan compounds of the present invention increase the N-I point and double refractive index (Δn) of the liquid crystal compositions which contain these compounds without affecting the viscosity and threshold voltage Vth of such compositions.

The tolan compounds of the present invention can increase the N-I point of a liquid crystal composition which contain these compounds without significantly affecting the viscosity and threshold voltage Vth. The tolan compounds can also decrease the viscosity of the liquid crystal composition and increase the double refractive index of the composition. The liquid crystal composition containing the tolan compound of the present invention has excellent properties as a liquid crystal material. The liquid crystal display device using this liquid crystal composition has a wide temperature use-range and a wide visible angle. In addition, the tolan compounds of the present invention exhibit sufficient mutual solubility with various compounds, which permits the tolan compounds to be used as a constituent of liquid crystal compositions in combination with many liquid crystal materials. Therefore, the tolan compounds of the present invention are useful for improving the properties of the liquid crystal compositions.

Obviously, numerous modifications and variations of the present invention are possible in light of the above teachings.

It is therefore to be understood that, within the scope of the appended claims, the invention may be practiced otherwise than as specifically described herein.

What is claimed is:

1. A tolan compound represented by the following formula (Ia):

(Ia)

wherein $A_1$ represents a phenyl group which is substituted by an alkyl group having 1–10 carbon atoms at the 4 position thereof or a cyclohexyl group which is substituted by an alkyl group having 1–10 carbon atoms at the 4 position thereof and R represents an alkyl group having 1–10 carbon atoms.

2. A tolan compound represented by the following formula (Ib):

(Ib)

wherein $B_1$ represents a single bond or and $A_2$ represents an alkyl group having 1–10 carbon atoms or an alkoxy group having 1–10 carbon atoms.

3. A tolan compound represented by the following formula (Ic):

(Ic)

wherein $B_2$ represents a group —CO—O— or —O—CO—, $A_3$ represents a cyclohexyl group which is substituted by an alkyl group having 1–10 carbon atoms at the 4 position thereof when $B_2$ is a group —CO—O— or represents a group represented by the following formula when $B_2$ is a group —O—CO—:

wherein Y represents a hydrogen atom or a halogen atom, Z represents an alkyl group having 1 to 10 carbon atoms or a halogen atom, and R represents an alkyl group having 1 to 10 carbon atoms.

4. A liquid crystal composition comprising the tolan compound of claim 1.

5. A liquid crystal composition comprising the tolan compound of claim 2.

6. A liquid crystal composition comprising the tolan compound of claim 3.

7. A liquid crystal display device using the liquid crystal composition according to claim 4.

8. A liquid crystal display device using the liquid crystal composition according to claim 5.

9. A liquid crystal display device using the liquid crystal composition according to claim 6.

* * * * *